United States Patent [19]

Komiya

[11] 4,046,149
[45] Sept. 6, 1977

[54] INSTRUMENT FOR REMOVING A FOREIGN SUBSTANCE FROM THE BODY CAVITY OF HUMAN BEING

[75] Inventor: Osamu Komiya, Hachioji, Japan

[73] Assignee: Olympus Optical Co., Ltd., Tokyo, Japan

[21] Appl. No.: 653,150

[22] Filed: Jan. 28, 1976

[30] Foreign Application Priority Data

| Jan. 31, 1975 | Japan | 50-14525 |
| Jan. 31, 1975 | Japan | 50-14526 |
| Jan. 31, 1975 | Japan | 50-14527 |
| Jan. 31, 1975 | Japan | 50-14528 |

[51] Int. Cl.² ............................................ A61B 17/22
[52] U.S. Cl. .................................... 128/328; 294/100
[58] Field of Search ................ 128/6, 7, 321, 325, 128/328; 294/99 R, 100

[56] References Cited

U.S. PATENT DOCUMENTS

| 1,127,948 | 2/1915 | Wappler | 128/328 X |
| 1,556,355 | 10/1925 | Roney | 128/6 |
| 1,612,697 | 12/1926 | Cecil | 128/328 UX |
| 2,599,662 | 6/1952 | Rosenbaum | 128/6 |
| 2,943,626 | 7/1960 | Dormia | 128/328 |
| 3,108,593 | 10/1963 | Glassman | 128/328 |
| 3,958,576 | 5/1976 | Komiya | 128/346 |

Primary Examiner—Channing L. Pace

[57] ABSTRACT

An instrument is adapted to be inserted through an endoscope channel into the body cavity of the human being together with an endoscope and remove a foreign substance such as polyp and stone within the body cavity of the human being. The instrument has trap means separable from the elongated tubular instrument body and the trap means are left within the body cavity of the human being, while being supported from the forward end of the supporting wire introduced into the body cavity of the human being together with the tubular instrument body, after they trap the foreign substances. The trapped foreign substances are drawn out through a supporting wire from within the body cavity of the human being together with the trap means when the endoscope is withdrawn from within the body cavity of the human being.

7 Claims, 17 Drawing Figures

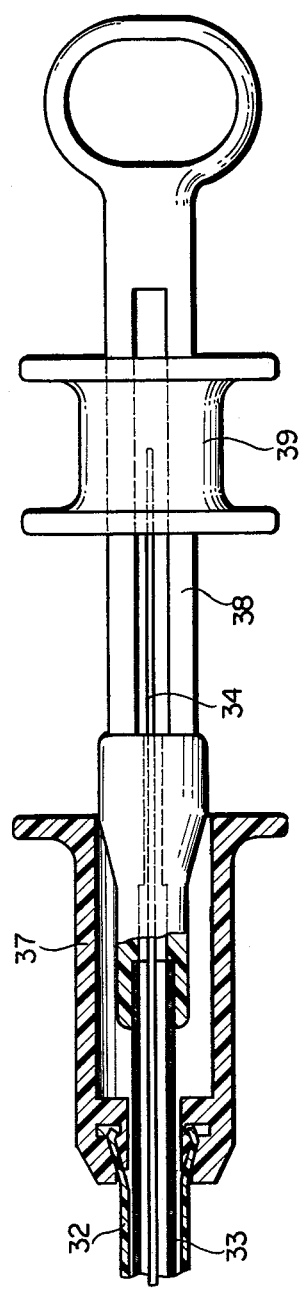

F I G. 7
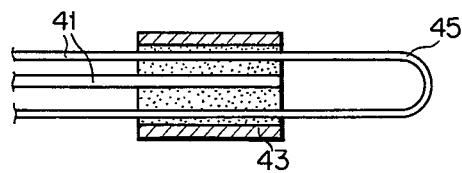
F I G. 8
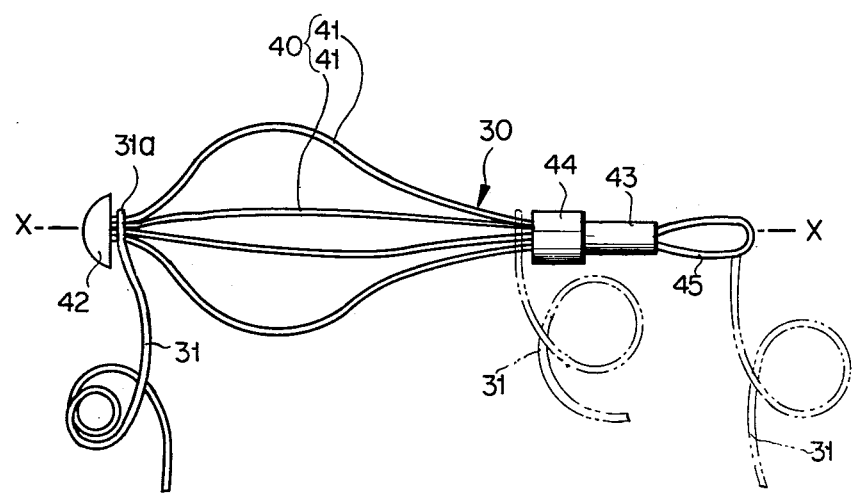

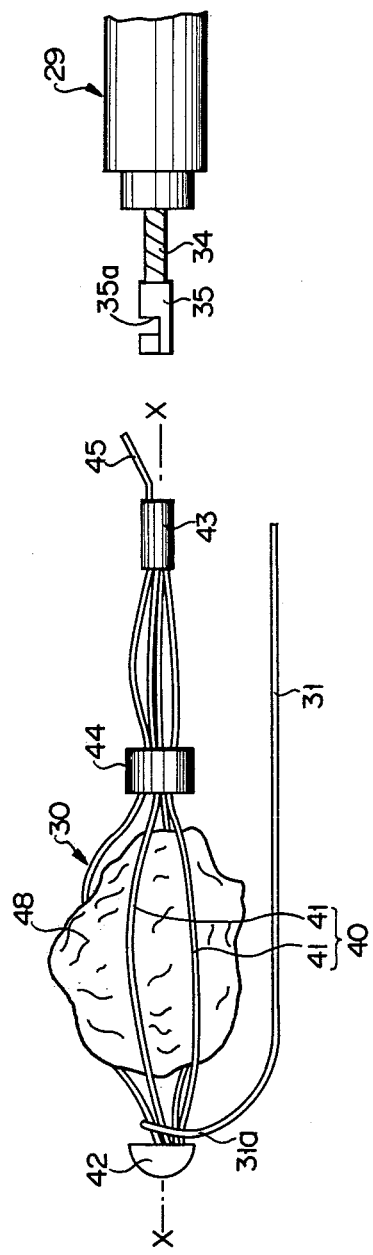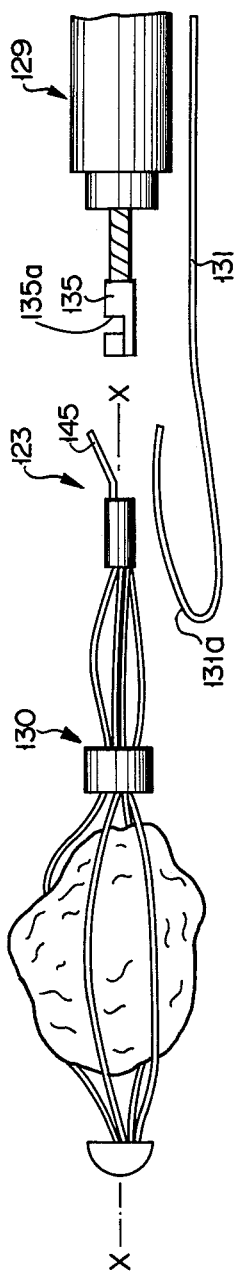
FIG. 9
FIG. 10

F I G. 12
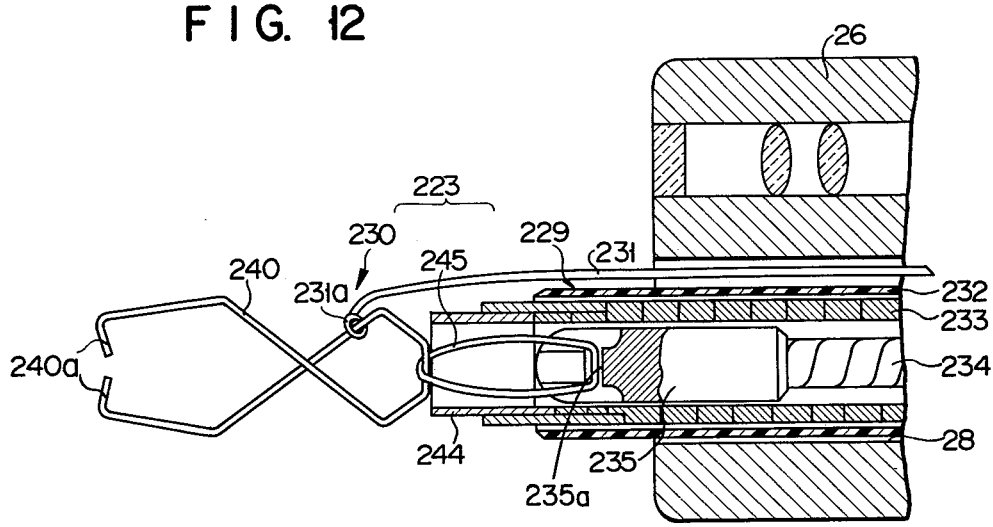
F I G. 13
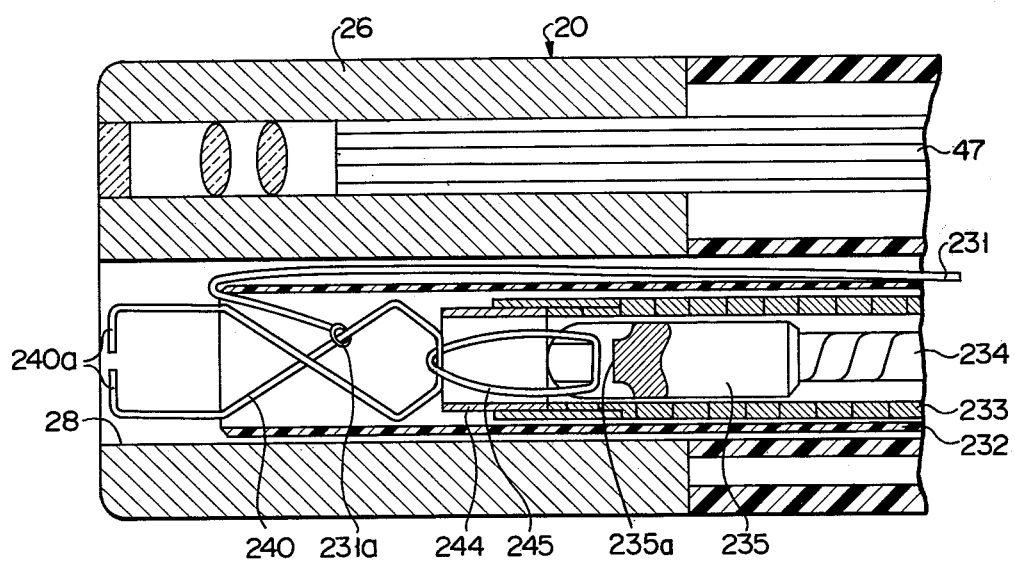

F I G. 17
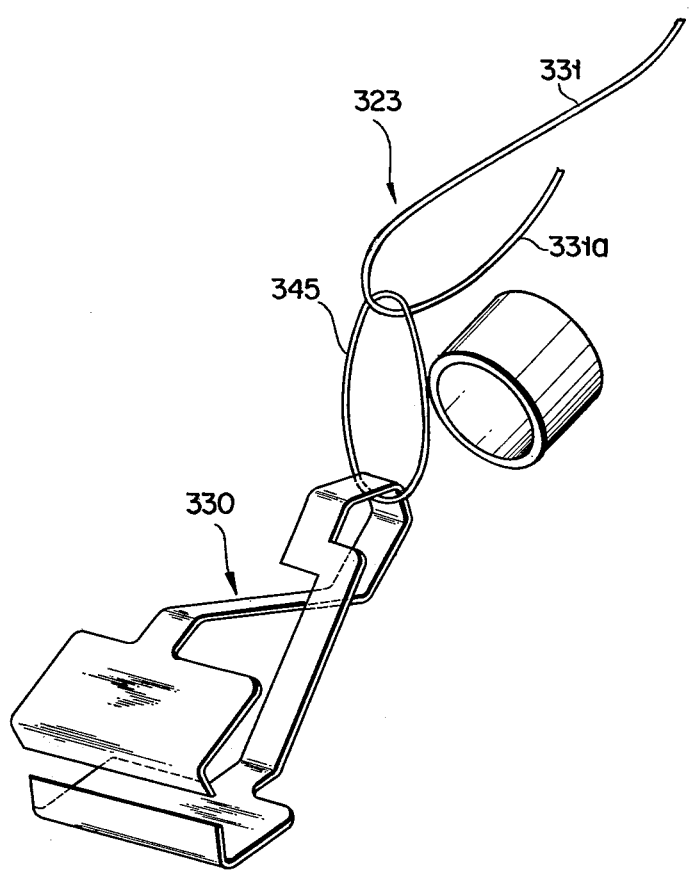

INSTRUMENT FOR REMOVING A FOREIGN SUBSTANCE FROM THE BODY CAVITY OF HUMAN BEING

BACKGROUND OF THE INVENTION

This invention relates to an instrument adapted to be inserted through an endoscope channel into the body cavity of the human being together with an endoscope and remove a foreign substance such as polyp, stone etc. outside of the body cavity of the human being.

A variety of foreign substance removing instruments are found in the art and in these instruments the head section of the instrument i.e., trap means for trapping the foreign substance such as a polyp is fixed to the forward end of the instrument body which is passed through an endoscope channel. When any foreign substance such as a polyp is found during the observation of the body cavity, it is removed away from the body cavity by a suitable resecting instrument and trapped by the trap means. When the foreign substance is removed outside of the body cavity, it is required that the endoscope per se be removed from within the body cavity of the human being. The endoscope channel is small enough to permit a slender body of the instrument to be passed therethrough and in contrast the foreign substance is relatively large in size. It is therefore impossible to withdraw the instrument from the endoscope channel with the foreign substance trapped by the trap means.

When a plurality of polyps are to be removed away from the body cavity for examination, the endoscope should be inserted into, and withdrawn from, the body cavity of the human being a corresponding number of times. It is not easy for the operator to insert the endoscope in proper place within the body cavity of the human being and such an operation imparts a severe pain to the patient. If, therefore, a plurality of polyps are to be removed outside the body cavity, a cumbersome operation is involved and the patient suffers from a pain while at the same time being exposed to a danger.

SUMMARY OF THE INVENTION

It is accordingly an object of this invention to provide an improved foreign substance removing instrument devoid of the above-mentioned drawbacks as encountered in the prior art and capable of easily and accurately trapping a plurality of foreign substances, while an endoscope is being inserted into the body cavity of a patient, and withdrawing the endoscope from within the body cavity without imparting any severe pain or danger to the patient after these foreign substances are all trapped by trap means.

According to the preferred embodiment of this invention trap means is inserted through an endoscope into the cavity of the human being in a manner that it is releasably anchored on the forward end portion of an elongated flexible instrument body. When any foreign substance is found within the body cavity of the human being, it is trapped by trap means and the trap means are released from the instrument body with the foreign substance trapped thereby. The so released trap means is supported through one end of a supporting wire and the other end of the supporting wire extends outside of the body cavity. When any further foreign substance is found within the body cavity of the human being, the endoscope remains there and only the instrument body is drawn out from the endoscope channel with the trapped foreign substance left within the body cavity together with the trap means supported through the supporting wire. Then, a new trap means is anchored on the forward end portion of the instrument body and a new supporting wire is connected to one end of the trap means. The instrument body is again inserted into the endoscope channel and the trap means on the forward end of the instrument body is directed toward the foreign substance. When the foreign substance is trapped by the trap means, the trap means is released as mentioned above and the trapped foreign substance is left within the body cavity of the human being. In this way, a plurality of foreign substances can be trapped by inserting and withdrawing only the instrument body through the endoscope channel in a manner that the endoscope remains inserted within the body cavity. After a corresponding number of foreign substances are all trapped by the trap means, the endoscope is withdrawn from the body cavity of the human being together with the trapped foreign substance. In consequence, it is not necessary to frequently insert and withdraw the endoscope into the body cavity of the human being and a simple and rapid operation can be effected without giving any severe pain to the patient. Since the endoscope remains located in the same position, any foreign substance found nearby can be positively trapped and withdrawn outside of the human body without missing it.

In some embodiment the trap means constitutes a cage formed by a plurality of wire elements, while in the other embodiment it constitutes a clip type with a pair of jaws which is provided in the form of a figure eight.

According to one embodiment of this invention the supporting wire is connected at one end to the trap means and one supporting wire is provided for each trap means. According to the other embodiment the supporting wire is bent to provide a hook on which all the trap means are anchored. In this case, a simple common supporting wire is provided. In the former case, the trap means is positively supported by the supporting wire and in the latter case the number of the supporting wires required can be saved.

BRIEF DESCRIPTION OF THE DRAWING

FIG. 3 is an enlarged view, partly in cross section and partly broken away, showing the base end section of the instrument in FIG. 1;

FIG. 7 is a cross-sectional view showing part of the cage type trap means;

FIG. 8 is an explanatory view showing a connection between the cage type trap means and the supporting wire;

FIG. 9 is a view showing a modified form of the cage type trap means;

FIG. 10 is a side elevational view showing a major part of an instrument according to a second embodiment of this invention;

FIGS. 12 to 15 are cross-sectional views showing the operative positions of a forward end section of an instrument according to the third embodiment of this invention;

FIG. 17 is a perspective, exploded view showing a major part of an instrument according to a fourth embodiment of this invention.

DETAILED DESCRIPTION OF THE PREFERRED EMBODIMENTS

Figure 1:
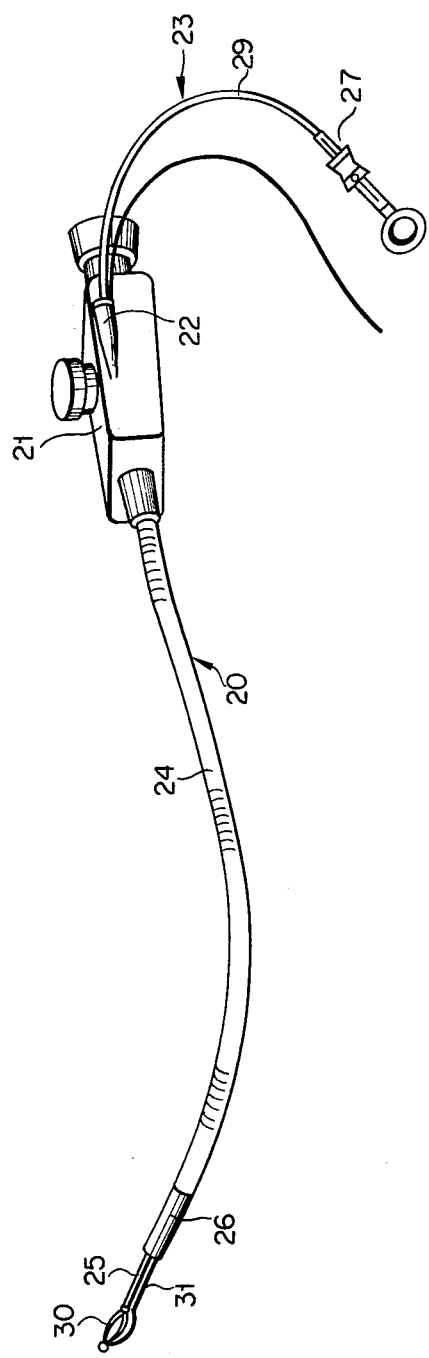
FIG. 1 is a perspective view showing a conventional endoscope in which a foreign substance removing instrument according to a first embodiment of this invention is incorporated.

FIG. 1 shows a conventional form of an endoscope 20. The endoscope 20 has a control unit 21 with an inlet 22. A foreign substance removing instrument 23 according to this invention is inserted from the inlet 22 of the control unit 21 into a channel (usually called a forceps channel) in the flexible tube 24 of the endoscope so that the forward section 25 thereof can extend from a distal end 26 of the flexible tube 24 with a base end section 27 of the flexible tube 24 left outside. (Any extra channel for the foreign substance removing instrument 23 can be used.)

The instrument 23 is so inserted into the body cavity of a human being and when a foreign substance such as a stone in the gall duct and ureter and polyp is observed it was removed by the instrument 23 outside the human body.

The instrument 23 comprises an elongated flexible instrument body 29, a trap means 30 for releasably trapping the foreign substance at the forward section 25 thereof and an elongated supporting wire 31 one end of which is connected to the trap means 30.

Figure 2:
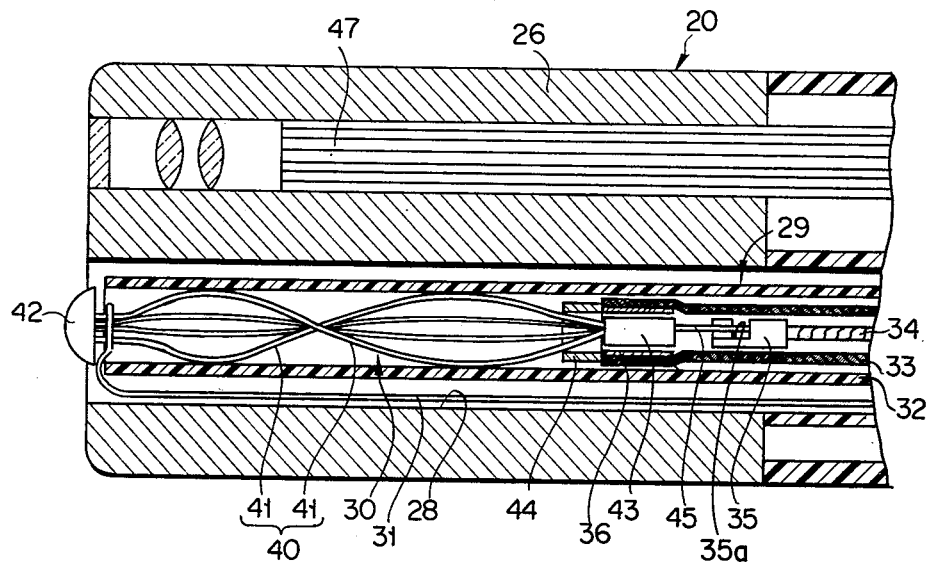
FIG. 2 is an enlarged, cross-sectional view, partly broken away, showing a forward end section of the instrument in FIG. 1.

As shown in FIG. 2 the flexible instrument body 29 has an outer flexible tube 32, an inner flexible tube 33 and a control wire 34, and a hook member 35 is anchored to the control wire 34. The hook member 35 has a cutout 35a at its side. A reinforcing ring 36 is fitted on the inner surface of the forward end portion of the inner tube 33 so as to impart a rigidity to the outer shape of the inner tube 33. The outer tube 32, inner tube 33 and control wire 34 can be slidably and axially moved relative to each other by operating them at the base end section side of the flexible tube 24. In FIG. 3 a socket like holding member 37 is provided at the base end portion of the outer tube 32 and an operating member 38 is provided at the base end portion of the inner tube 33 so that a part thereof is slidably received in a bore of the holding member 37. A sliding member 39 is provided at the base end portion of the control wire 34 and is axially and slidably movable on the operating member 38. The outer flexible tube 32, inner flexible tube 33 and control wire 34 can be axially and slidably moved relative to each other by operating them by the fingers of the operator. It is to be noted that the construction of the base end section 27 per se of the flexible tube 24 does not constitute a main part of this invention.

The trap means 30 is of a cage type and a cage 40 is formed by connecting together the wire elements 41, each consisting of a plurality of filament wires, by a head connector 42 and base connector 43. Both the ends of the cage 40 are rigidly secured by the head connector 42 and base connector 43 respectively. The intermediate portions of the wire elements have a tendency to be normally radially outwardly curved in a direction of the axis X—X in FIG. 8 to provide a space, i.e., a cage, capable of trapping any foreign substance therein. A clamp ring 44 is fitted over the wire elements and is slidably movable in the axial direction and some of the wire elements 41 extend rearwardly beyond the base connector 43 to provide a loop which serves as an anchoring member 45. The anchoring member 45 is releasably anchored to the cutout 35a of the hook member 35. The wire elements 41 are brazed or soldered at the base connector 43 and at the head connector 42.

A forward end 31a of the elongated supporting wire 31 is fixed to the wire elements 41 in the neighborhood of the head connector 42. The supporting wire 31 is passed through the channel 28 in the flexible tube body 29 and the base end of the supporting wire 31 is left outside the inlet 22 of the central unit 21. The forward end 31a of the supporting wire 31 may be fixed, as indicated by a chain line in FIG. 8, in the neighborhood of the base connector 41, at the loop-like anchoring member 45 or at any other portion on the trap means.

The operation of the removing instrument will now be described below.

Figure 4:
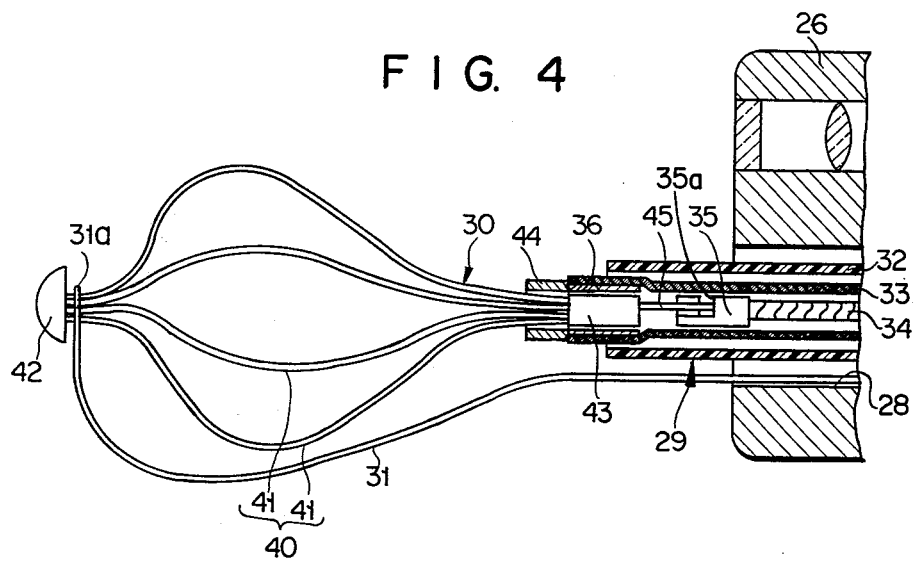
FIG. 4 is an enlarged, cross-sectional view, similar to FIG. 2, showing that a cage type trap means are curved radially outwardly.
Figure 5:
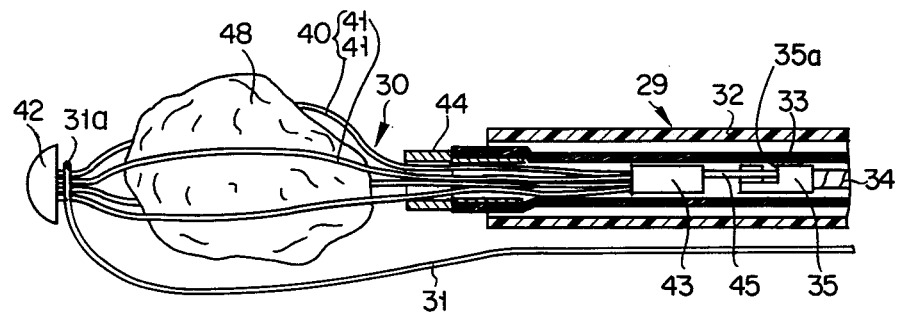
FIG. 5 is an enlarged, cross-sectional view, partly broken away, showing the manner in which a foreign substance is trapped by the cage type trap means.
Figure 6:
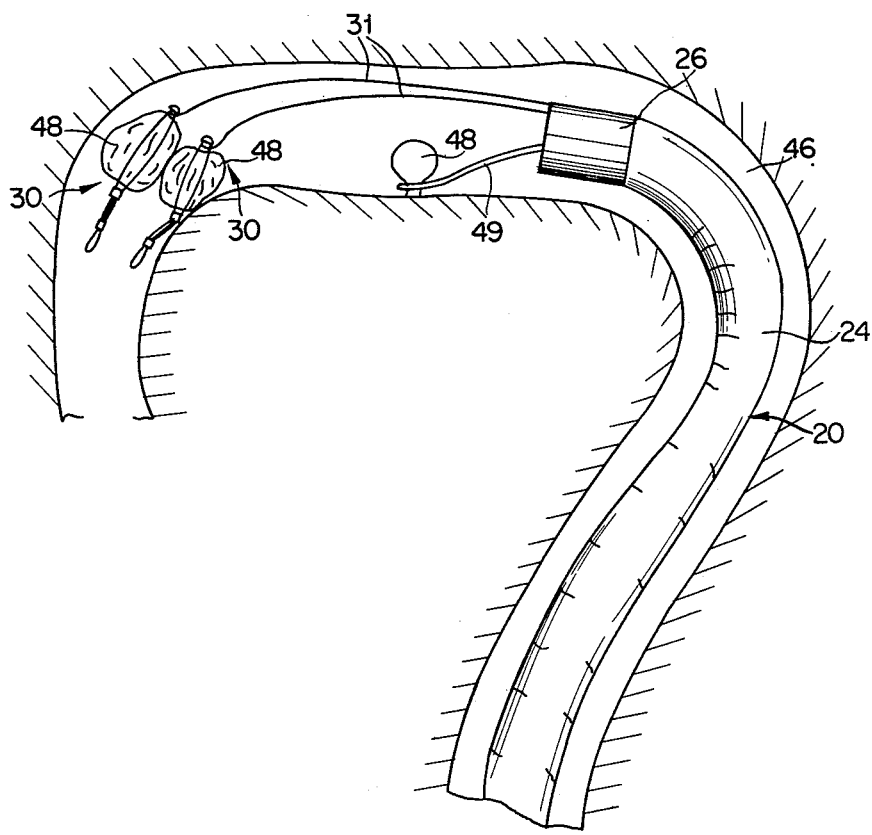
FIG. 6 is an explanatory view showing the manner in which foreign substances are trapped within the body cavity of a human being using the instrument.

The flexible tube 24 of the endoscope 20 is inserted into a body cavity 46 of a human being (see FIG. 6). The body cavity is observed through an optical means 47 including a fiber bundle which is incorporated in the endoscope. The instrument is inserted into the endoscope channel in such a manner that the trap means 30 is inserted until the head connector 42 is brought into contact with the end surface of the outer tube. The insertion of the instrument into the endoscope can be effected when and before any foreign substance is observed in the body cavity of the human being. Since the wire elements 41 constituting the cage 40 have a sufficient flexibility, they are smoothly passed through the outer tube 32. When any foreign substance or affected area 48 including a polyp is observed in the body cavity 46 of the human being, the trap means 30 is projected from the distal end 26 as shown in FIG. 4 through a manual operation at the base end section of the removing instrument. As a result, the wire elements are radially outwardly curved by their own self-resiliency to provide the cage 40. When, for example, any polyp 48 is observed in the body cavity of the human being, it is cut away by a known resecting means 49. Thereafter, the substance 48 is trapped, while observing the body cavity through the endoscope, by the radially outwardly curved trap means 30 as shown in FIG. 5. Since the cage 40 is constituted by the flexible wire elements 41, even if the foreign substance 48 is either hard or somewhat large, it can be easily trapped by the cage 40.

If in FIG. 5 only the control wire 34 is moved rightward, the cage 40 is pulled or squeezed into the inner tube 33, the clamp ring 44 is relatively axially moved slidably leftward due to the ring 44 held at the forward end of the inner tube to cause the cage 40 to be shortened. As a result, the substance 48 is caught by the wire elements 41 and positively trapped by the cage 40. Once the ring 44 is so slidably moved, it is held at that position since the ring 44 is frictionally contacted with the wire elements 41.

After the substance 48 is tightly caught by the trap means 30, the control wire 34 is pushed leftward so that the hook member 35 is moved away from the end of the inner tube 33, and the trap means 30 is released from the cutout 35a of the hook member 35. The so released trap means 30 is dropped within the body cavity 46 with the foreign substance 48 trapped thereby and, as shown in FIG. 6, it is temporarily anchored within the body cavity 46 through the supporting wire 31 connected to the trap means 30.

When any further foreign substance 48 is observed, only the instrument body 29 of the instrument is drawn out from the endoscope channel 28 and another trap means 30 is mounted on the end portion of the instrument body 29. Another supporting wire 31 is also connected to the trap means 30. These members are likewise inserted within the endoscope channel 28. The foreign substance 48 can be trapped by the same operation. The trapped substance 48 is likewise anchored within the body cavity 46 through the supporting wire 31. Thus, a plurality of foreign substances can be sequentially trapped in the manner that the endoscope remains inserted into the body cavity.

When the observation of the body cavity, as well as the trapping of the foreign substance, is completed, the endoscope 20 is drawn out from the body cavity 46 of the human being. If at this time a plurality of foreign substances are involved, such substances are also drawn out from the body cavity together with the endoscope.

When the loop-like anchoring member 45 of the trap means 30 is engaged with the hood member 35, disengagement of the anchoring member 45 from the hook member 35 is prevented, since the inner diameter of the inner tube 33 is small. When, however, the anchoring member 45, together with the hook member 35, is pushed out into the body cavity, it is desirable that it be easily disengaged from the cutout 35a of the hook member 35. In a modification shown in FIG. 9 the anchoring member 45 has a tendency to be resiliently urged sidewise with respect to an axis X—X of the trap means 30. When, therefore, the anchoring member 45 is pushed out into the body cavity, it can be automatically disengaged, under its own elastically urging force, from the cutout 35a of the hook member 35, unless the hook member 35 is vibrated in a sidewise direction.

Figure 11:
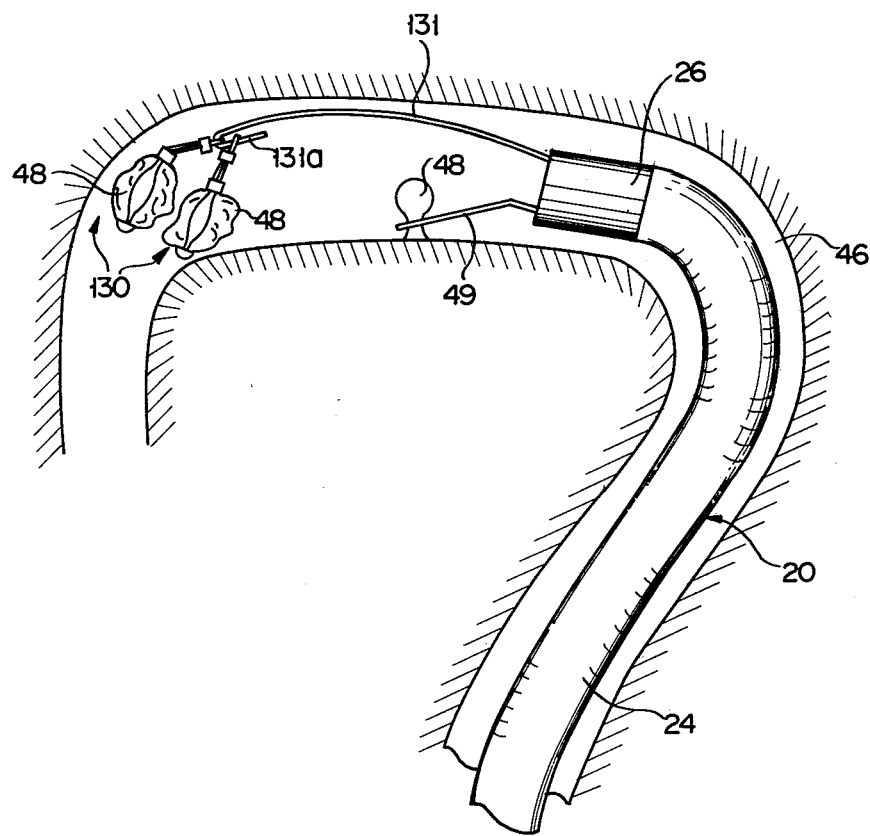
FIG. 11 is an explanatory view showing the manner in which foreign substances are trapped within the body cavity of a human being using the instrument according to the second embodiment of this invention.
Figure 14:
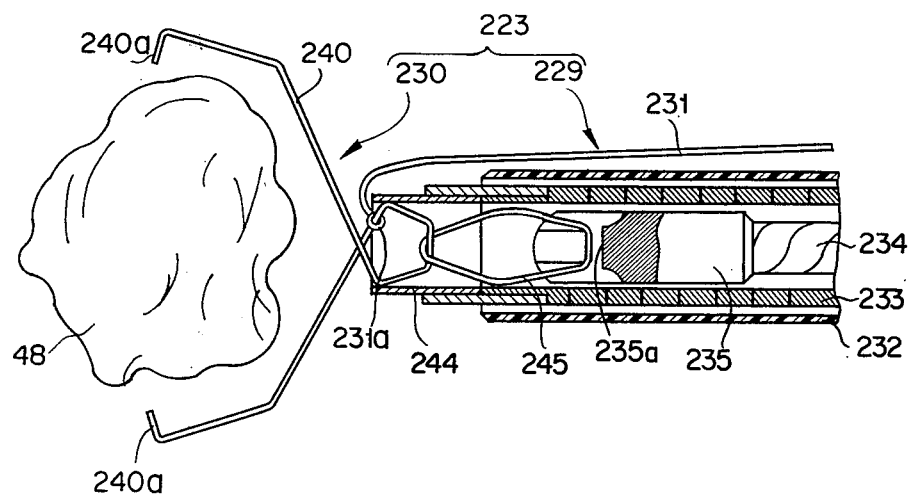

FIGS. 10 and 11 show a foreign substance removing instrument 123 according to a second embodiment of this invention, which is substantially similar in its construction to the first embodiment. A cage-like trap means 130 corresponds to the trap means 30 and an anchoring member 145 corresponds to that of the modification if FIG. 9. An instrument body 129 corresponds to the instrument body 29, but only the forward portion thereof is shown in FIG. 10. The second embodiment is different from the first embodiment in that a supporting wire 131 of a foreign substance removing instrument 123 has a hook-like forward end 131a. The supporting wire 31 of the first embodiment is inserted into the endoscope channel with the forward end 31a fixed in proper place on the trap means 30 as shown in FIG. 8. The supporting wire 131 of the second embodiment, on the other hand, is inserted into the endoscope channel separately from the trap means 130.

The operation of trapping a foreign substance 48 by the trap means 130, while observing the body cavity, is substantially the same as in the first embodiment. In the second embodiment, on the other hand, the anchoring member 145 is disengaged from the cutout 135a of the hook member 135 and the hook-like forward end 131a of the supporting wire 131 is adapted to be anchored on the anchoring member 145 as shown in FIG. 11 after the trap means 130 is dropped within the body cavity. In this case, the distal end of the endoscope is moved in a conventional method for anchoring and the forward end 131a of the supporting wire 131 is so controlled that it is brought into an anchoring engagement with the anchoring member 145.

When any further foreign substance is found in the body cavity of the human being, only the instrument body 129 is drawn out from the endoscope channel, another trap means is mounted on the forward end of the instrument body and again inserted through the instrument body into the endoscope channel. In this case, no extra supporting wire is necessary. It is because that, when the trap means is dropped within the body cavity after it traps the foreign substance, the trap means is anchored on the forward end 131a of the supporting wire 131 as shown in FIG. 11. Since in this way a plurality of trap means are anchored on the common supporting wire 131, it is not necessary to prepare a plurality of supporting wires 131.

When the observation of the body cavity, as well as the trapping of the foreign substance, is completed, the endoscope is drawn out from the body cavity of the human being, together with the supporting wire 131, with the plurality of trap means anchored on the forward end 131a of the supporting wire 131.

FIGS. 12 to 16 show a foreign substance removing instrument 223 according to the third embodiment of this invention. An instrument body 229 of the instrument 223 is substantially similar in construction to the instrument body 29 of the first embodiment and includes an outer tube 232, inner tube 233, control wire 234 and a hook member 235 secured to the forward end of the control wire 234. The instrument body 229 is adapted to be inserted into a channel 28 of an endoscope 20. The base end section of the instrument body 229 is substantially similar in construction to that of the first embodiment and is therefore omitted.

The third embodiment of this invention is different from the first embodiment in that a trap means 230 is of a clip type. The trap means 230 comprises a clip member 240 with a pair of jaws 240a which is formed by bending a plate into the form of a figure "eight", an anchoring loop 245 anchored on the rear end of the clip member 240 and a control ring 244 fitted over the anchoring loop 245. A forward end 231a of a supporting wire 231 is tied to the clip member 240. The supporting wire 231 is passed through the endoscope channel 28 along the instrument body 229 with the base end thereof outside of the endoscope.

The clip type trap means 230 is such that the anchoring loop 245 is releasably engaged with the hook member 235, and it is substantially similar in its function to the trap means of the preceding embodiment. When in FIG. 13 the endoscope is inserted into the body cavity of the human being, the trap means 230 of the foreign substance removing instrument 223 is maintained in a manner to be sufficiently withdrawn within the endoscope channel 28. When any foreign substance is to be trapped, the clip member 240 is projected from the endoscope channel 28 toward the body cavity. FIGS. 12 and 13 correspond to FIGS. 4 and 2, respectively.

When in FIG. 12 the control wire 234 only is pulled leftward a predetermined distance, the control ring 244 is brought into pressure contact with the rear of the clip member 240 to cause the pair of jaws 240a to be forcibly swung wide open. As a result, the clip member 240 can clip the foreign substance 48.

Figure 15:
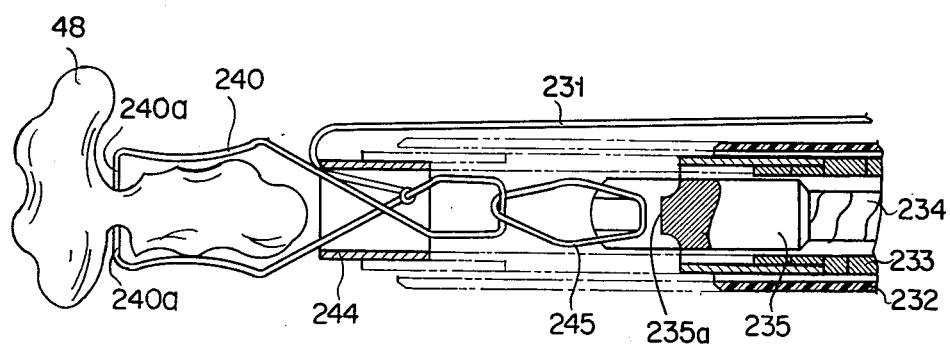
Figure 16:
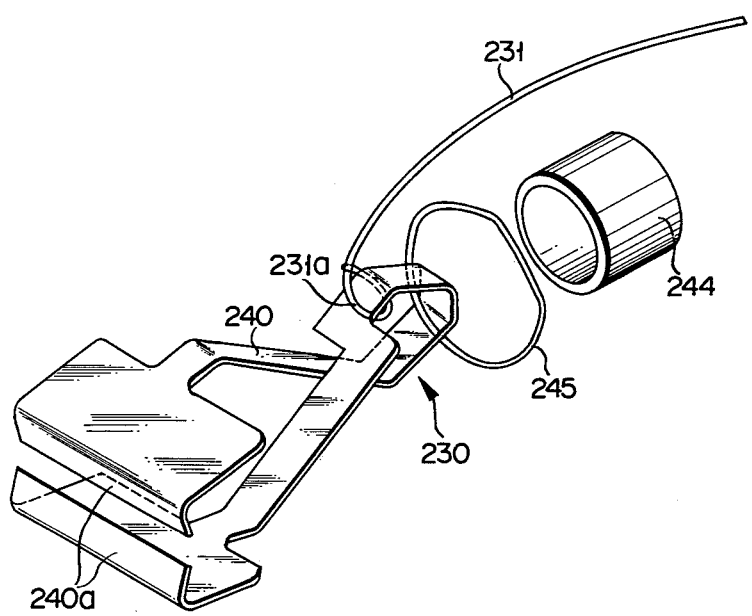
FIG. 16 is a perspective, exploded view explaining a connection between the clip type trap means and the supporting wire.

When the wire 234 is further pulled rightward as shown in FIG. 15, the clip member 240 is further inserted midway of the control ring 244 to cause the pair of jaws 240a to be forcibly closed. As a result, the foreign substance 48 is forcibly clipped. Thereafter, the control wire 234 is pushed leftward so that the hook member 235 is projected outside of the inner tube 233. By so doing the anchoring loop 245 can be disengaged from the cutout 235a of the hook member 235. In this case, the distal end of the endoscope will be so operated that the hook member 235 is vibrated sideway for disengagement of the anchoring loop 245 from the hook member 235.

When the trap means 230 is separated from the instrument body 229, it is dropped within the body cavity. Since the forward end 231a of the supporting wire is secured to the clip member 240, the trap means 230 is temporarily anchored, by the wire 231, within the body cavity of the human being.

If another foreign substance is found during the observation of the body cavity, only the instrument body 229 is drawn out from the endoscope channel. A new clip type trap means is fixed on the forward end of the instrument body and a forward end of a new control wire is fixed on the clip member of the trap means. These members are again inserted into the endoscope channel. This operation is substantially the same as the first embodiment.

Although the clip member 240 is shown in the form of the figure "eight", any other shape, for example, a V-shape can be employed as the clip member 240.

FIG. 17 shows a foreign substance removing instrument 323 according to a fourth embodiment of this invention. The instrument body and trap means of this embodiment are exactly the same as those of the third embodiment. This embodiment is different from the third embodiment in that the supporting wire 331 has a hook-like forward end 331a. The hook-like forward end 331a of the supporting wire 331 is anchored on an anchoring loop 345 of the trap means 330. The relation in which the hook-like forward end 331a is engaged with the loop 345 is substantially the same as that in the second embodiment. Since in this embodiment the supporting wire 331 can support a plurality of clip-like trap means, it will be understood that, even when a plurality of foreign substances are removed from within the body cavity, the supporting wire 331 can be served as a common supporter for the trap means.

The preceding embodiments are so constructed that, even when a plurality of foreign substances are to be removed from within the body cavity of the human being, they are trapped one by one by the respective trap means, that the trap means are anchored through the respective supporting wires or the single common supporting wire within the body cavity of the human being and that after the observation of the body cavity as well as the trapping of all the foreign substances is completed the foreign substances are drawn out, together with the endoscope, toward the outside. According to this invention, therefore, no cumbersome operation as encountered in drawing out the endoscope each time the foreign substance is trapped is necessary and furthermore the trapping of the foreign substance can be rapidly effected with accuracy. This imparts no excessive pain to the patient and there is less chance that the patient will be in danger.

Although in the above-mentioned embodiment the supporting wire is inserted together with the instrument body into the endoscope channel, it is possible to insert the supporting wire, in the case of the first and third embodiments, between the inner and outer tubes of the instrument body and it is also possible to insert the common supporting wire into another endoscope channel as distinct from the endoscope channel into which the instrument body is inserted.

What is claimed is:

1. An instrument inserted through a channel of an endoscope for trapping a foreign substance, such as a polyp or stone, and removing it outside of the body cavity of a human being, comprising:

an elongated flexible instrument body having an outer tube, an inner tube, and a control wire axially and slidably inserted into the inner tube and having a hook member at one end thereof, said hook member having a cutout at its side;

trap means having a loop-like anchoring member releasably anchored within said cutout of the hook member, said anchoring member being detachable from the cutout of the hook member when the hook member is moved out of the inner tube, thereby releasing the trap means from the instrument body;

a ring member slidably moved and fitted over the trap means for squeezing the same; and a supporting wire one end of which supports the trap means released from the instrument body, the other end of which passes through the channel of the endoscope and extends outside thereof.

2. The instrument according to claim 1, in which said trap means includes a cage made of a plurality of wire elements, the ends of said cage being rigidly secured by a head connector and a base connector respectively; and said one end of the supporting wire being tied to the wire elements in the neighborhood of the head connector.

3. The instrument according to claim 1, in which said trap means includes a cage made of a plurality of wire elements, the ends of said cage being rigidly secured by a head connector and a base connector respectively; some of said wire elements extending rearwardly beyond the base connector to provide a loop which serves as said anchoring member.

4. The instrument according to claim 3, in which said one end of the supporting wire is tied to said anchoring member.

5. The instrument according to claim 3, in which said anchoring member has a tendency to be resiliently urged sidewise with respect to the axis of the trap means.

6. The instrument according to claim 1, in which said trap means includes a clip member in the form of a figure eight having one loop openable, and said anchoring member of the trap means is made of a looped wire.

7. The instrument according to claim 1, in which said one end of the supporting wire is formed to have a hook on which a plurality of trap means are anchored.

* * * * *